(12) United States Patent
Abraham

(10) Patent No.: US 8,038,622 B2
(45) Date of Patent: Oct. 18, 2011

(54) WIRED AND WIRELESS REMOTELY CONTROLLED ULTRASONIC TRANSDUCER AND IMAGING APPARATUS

(75) Inventor: Theodore P. Abraham, Baltimore, MD (US)

(73) Assignee: InnoScion, LLC, Baltimore, MD (US)

( * ) Notice: Subject to any disclaimer, the term of this patent is extended or adjusted under 35 U.S.C. 154(b) by 654 days.

(21) Appl. No.: 12/182,247

(22) Filed: Jul. 30, 2008

(65) Prior Publication Data
US 2009/0036780 A1 Feb. 5, 2009

Related U.S. Application Data

(60) Provisional application No. 60/953,861, filed on Aug. 3, 2007.

(51) Int. Cl.
*A61B 8/13* (2006.01)
(52) U.S. Cl. ...................... 600/459; 600/444
(58) Field of Classification Search .............. 600/382, 600/386–392, 437, 440–447, 459–463; 128/903
See application file for complete search history.

(56) References Cited

U.S. PATENT DOCUMENTS

| | | | |
|---|---|---|---|
| 3,556,079 A | | 1/1971 | Omizo |
| 3,893,449 A | * | 7/1975 | Lee et al. ................ 600/459 |
| 4,341,120 A | * | 7/1982 | Anderson ................ 73/618 |
| 4,483,344 A | * | 11/1984 | Atkov et al. ............ 600/459 |
| 4,757,823 A | * | 7/1988 | Hofmeister et al. ......... 600/437 |
| 4,869,258 A | | 9/1989 | Hetz |
| 5,159,931 A | * | 11/1992 | Pini ........................ 600/443 |
| 5,381,794 A | * | 1/1995 | Tei et al. ................. 600/459 |
| 5,454,373 A | | 10/1995 | Koger et al. |
| 5,465,724 A | | 11/1995 | Sliwa, Jr. et al. |
| 5,598,845 A | * | 2/1997 | Chandraratna et al. ....... 600/459 |
| 5,701,901 A | | 12/1997 | Lum et al. |
| 5,823,963 A | * | 10/1998 | Takeuchi ................. 600/443 |

(Continued)

FOREIGN PATENT DOCUMENTS

CA 2 376 103 1/2001

(Continued)

OTHER PUBLICATIONS

International Search Report corresponding to International Application No. PCT/US2007/081185 dated Jul. 10, 2008.

*Primary Examiner* — Francis Jaworski
(74) *Attorney, Agent, or Firm* — PCT Law Group, PLLC (57) ABSTRACT

A remotely manipulatable transducer element or linear transducer array for use with a remote work station including a display permits an operator of an ultrasound system to be remotely located from a patient. The transducer or linear transducer array comprises an assembly within a housing for fixation to a human body and intended to be placed one time and then remotely manipulated in directions of rotation, twist, and linearly in first and second perpendicular directions within a plane parallel to the surface of the human body under study. In one embodiment, the housing comprises a motor and a linear transducer array which are mounted to a rotor of the motor via an optional gear assembly for rotation, for example, in a range of 180 degrees so that multiple planes of imaging can be obtained, for example, of a heart or other body organ. The remotely manipulatable transducer or transducer array assembly may comprise a wireless transceiver having a unique identifier for communication with one or more work stations, each having a unique identifier.

26 Claims, 8 Drawing Sheets

U.S. PATENT DOCUMENTS

| | | | |
|---|---|---|---|
| 5,882,300 A * | 3/1999 | Malinouskas et al. | 600/300 |
| 5,997,497 A | 12/1999 | Nita et al. | |
| 6,056,692 A * | 5/2000 | Schwartz | 600/443 |
| 6,149,598 A | 11/2000 | Tanaka | |
| 6,527,718 B1 * | 3/2003 | Connor et al. | 600/439 |
| 6,558,326 B2 | 5/2003 | Pelissier | |
| 6,572,551 B1 | 6/2003 | Smith et al. | |
| 6,858,008 B2 * | 2/2005 | Li et al. | 600/437 |
| 7,118,531 B2 | 10/2006 | Krill | |
| 7,127,401 B2 | 10/2006 | Miller | |
| 7,695,437 B2 * | 4/2010 | Quistgaard et al. | 600/446 |
| 7,731,662 B2 * | 6/2010 | Anderson et al. | 600/459 |
| 2002/0065464 A1 | 5/2002 | Murphy et al. | |
| 2005/0090709 A1 | 4/2005 | Okada et al. | |
| 2006/0106315 A1 | 5/2006 | Edens | |
| 2007/0066894 A1 | 3/2007 | Bartol et al. | |

FOREIGN PATENT DOCUMENTS

| | | |
|---|---|---|
| CA | 2 376 103 | 1/2002 |

* cited by examiner

WIRED AND WIRELESS REMOTELY CONTROLLED ULTRASONIC TRANSDUCER AND IMAGING APPARATUS

This application claims the benefit of priority to provisional U.S. Application Ser. No. 60/953,861, filed Aug. 3, 2007, incorporated herein by reference as to its entire contents.

TECHNICAL FIELD

The technical field of the several embodiments of a wireless ultrasonic transducer relates generally to the field of ultrasound imaging methods and apparatus and, more particularly, to embodiments thereof wherein the ultrasonic arrays and imaging apparatus may be affixed to a patient and be remotely controlled as to rotation, linear movement, pitch and, generally, direction and depth of imaging, in addition to other control aspects and features, such that imaging and control thereof may be conducted remotely from the patient with minimal invasion of patient privacy.

BACKGROUND

Ultrasonic imaging is known in the art and systems typically involve the use of hand-held or temporarily affixed ultrasonic transducer arrays that may be controlled, for example, as to on/off, mode, focus control, depth control and the like. The user applies a small amount of ultrasound gel to a region of interest, holds and moves the ultrasound transducer from one location of the patient to another within the region, the unit being wired to a console, typically including a display. Ultrasound is a biologically safe and non-radiating form of energy that can provide detailed anatomic and, in some cases, functional images. It is known in the art of transesophageal echocardiography (imagery of the heart) to provide a multi-plane transducer that can image in planes in a 180 degree range.

It is also known, for example, in the telecommunications arts to remotely transmit images such as photographic images from a source such as a cellular telephone device to a receiving cellular telephone or other telecommunications device. For example, a doctor may transmit a digital image to another doctor by attaching the image to an email. An x-ray machine located in a remote laboratory may capture an image of a broken bone, and the technician may immediately transmit the image to an orthopedic unit of a hospital for analysis. Cellular telephone devices are now capable of capturing and transmitting moving images, including movies with associated sound, for personal enjoyment.

U.S. patent application Ser. No. 11/782,991, filed Jul. 25, 2007, entitled "Image Guided Catheters and Methods of Use," of the same inventor describes a plurality of embodiments of an image guided catheter that may be used, for example, to image an area of the thoracic cavity such as the heart or other region of interest and deliver medication, treatment and the like accompanied by ultrasonic and other imaging with an ultrasonic array mounted towards a distal end of a catheter. The catheter is provided with a plurality of lumen running from a proximal to the distal end. Interventional, diagnostic or therapeutic devices may be inserted via a sheath to the region of interest.

U.S. Pat. No. 7,118,531, issued Oct. 10, 2006, to Krill describes an ingestible medical payload carrying capsule with wireless, e.g. ultrasonic, communication to transducers placed on a patient. The capsule may deliver medication or contain imaging apparatus such as an optical camera and/or a transducer with a pulse driver for internal acoustic pulse illumination and external high resolution sonogram imaging and detection.

United States Patent Application, US 2002/0065464, published May 30, 2002, describes an imaging device including a wireless mobile unit. Ultrasonic imaging devices and viewing apparatus are large and bulky apparatus. The described imaging device allows an operator to move freely throughout the operating arena, without being tangled within cords and allowing the patient to remain relatively undisturbed while simultaneously allowing the operator full access to the entire patient's body.

United States Patent Application, US 2007/0066894, published Mar. 22, 2007, describes a remote wireless control device for an ultrasound machine and method. The remote wireless control device includes a subset of controls present on larger apparatus including a sonogram display. A smaller mobile unit communicates with the larger unit and may be more easily used bed-side than the larger apparatus.

Each of the above-identified patents and patent applications should be deemed to be incorporated by reference herein as to their entire contents.

SUMMARY OF EMBODIMENTS AND ASPECTS

This summary is intended to introduce, in simplified form, a selection of concepts that are further described in the Detailed Description and depicted in the drawings. This summary is not intended to identify key or essential features of the claimed subject matter, nor is it intended to be used as an aid in determining the scope of claimed subject matter. Embodiments and aspects described herein relate generally to embodiments and aspects and methods of use of a wired or wireless transducer array that may be remotely controlled to capture multiple image planes at a region of interest of a patient or victim and manipulated or moved to different locations on the skin surface without having to have an operator or large ultrasound system apparatus present at the site of the patient or victim (hereinafter, simply, patient).

In accordance with one embodiment, a transducer array unit for fixing to a patient's body is wireless (or wired) and communicates imaging data collected by a typically linear ultrasonic array by wireless (or wired) means to an external site where collected imaging data is displayed and may be viewed by an operator. One embodiment of a wireless transducer unit is very much like a probe that can be affixed to the body surface and its imaging functions controlled remotely, for example, by wireless radio telecommunication such as WiFi, Wimax, blue tooth or other radio frequency communication protocol. The wireless communication may also be ultrasonic, infrared or utilize other wireless communication frequencies. The wireless or wired link may be a local or long distance telecommunications link involving satellite transmission. The transducer may be any ultrasound transducer (mechanical, annular, phased array or linear array) and may be single or multi-dimensional. Each transducer array unit may have its own unique identification code which is communicated with each wireless or telecommunications transmission to a host site of ultrasound imaging processing, control and display. The unique code of the remotely manipulatable transducer array unit is used by a host ultrasound imaging remote site to communicate with it. The transducer array unit is, for example, battery powered and self-contained such that it may be worn by a patient with minimal invasion of the patient's privacy. It includes in primary part, ultrasonic transducer circuitry for transmitting and receiving ultrasonic waves, control leads for mode, depth, focus and the like as is known in the art but additionally includes control leads for controlling the movement of the transducer array and the direction of its transmission as well as image data transmission and control data reception circuitry. The transducer assembly thus contains a transducer array or element unit that is remotely manipulatable.

The patient may eat, sleep or, otherwise, function, for example, in or out of their hospital bed while the unit remotely views and transmits imaging data to the remote site. The unit of this embodiment fixed to the patient's body may comprise a linear array of transducers or a single transducer element that may be remotely controlled to rotate from one position to another, either clock-wise or counter-clock-wise to obtain a different planar view of the body part under analysis. The shape of the transducer unit may be round for multi-plane or square or rectangular for other transducers. The wireless transducer unit may function with a three dimensional imaging system allowing stereotactic and remote/robotic operation of devices delivered through or in conjunction with the unit as will be further described below. The transducer array or element may be fixed to a rotor and the rotor assembly and transceiver circuitry housed within a housing having for example a cylindrical shape with one side intended to be facing the patient's body. The flat side facing the body may have a layer of body impedance matching material complimentary to any gel application. A micromotor and optional associated gear assembly may incrementally rotate the transducer array or element, for example, through a range of 180 degrees. Its position may be remotely determined and stored in local or remote memory and/or displayed at the external remote control site. The size of the footprint of a housing for a remotely manipulatable transducer unit on a patient's body surface may be as small as 1 cm or as large as several centimeters in diameter (or length/width). Typical operating frequency of the ultrasonic transducer array or element may be between 200 kHz and 100 MHz depending on the clinical application. In addition to rotation, a linear transducer array may be adaptably mounted to a rotor shaft so that it may also redirect output sound waves within a range of 180 degrees within the patient's body at the given angle of rotation. A first transducer array or element may cooperate with a second transducer array unit situated inches away as a transmitter while the second device operates as a receiver and vice versa. The first and second transducer array units may separately provide image data of the same region of interest to a remote work station. The rotatable transducer embodiment may, for example, of circular or cylindrical shape and may be affixed to the body by a broad securing material that may be either adhesive or non-adhesive, such as a band or bandage of cloth or other fiber. No operator need be attendant at the patient site. Imaging data may be converted from analog to digital format and compressed before it is transmitted in accordance with well known standards to conserve transmission bandwidth. Typical ultrasonic imaging bandwidth requirements should be on the order of 1 MHz. If high levels of resolution are required, the bandwidth may exceed 5 MHz or, if low resolution is permitted, a 100 kHz bandwidth may suffice.

In yet another embodiment, the patient may be an out-patient and wear a battery-powered transducer array or transducer element apparatus that may be remotely monitored and manipulated via a telecommunications channel or by the out-patient via a cord to a remote control. Image data may be collected and stored locally in removable or accessible memory over time. The out-patient may visit their doctor and the memory contents unloaded rather than be remotely transmitted. On the other hand, the memory, when it reaches a predetermined fill capacity may transmit its contents via the transceiver to a remote work station for analysis. If a remote work station operator sees an extraordinary condition in ultrasound imagery, the out-patient may be warned by the operator's triggering a vibration or other alarm of such condition via a telecommunications or wireless link that the out-patient must see their doctor immediately.

The operator may continuously monitor, for example, from the remote site for signs of patient difficulty. For example, the development of a blood clot or other serious condition may be viewed remotely if the device is used in conjunction with, for example, a knee replacement operation.

The out-patient may control the transducer array or element themselves, for example, to deliver therapeutic ultrasound waves to a region of interest to them and so manipulate the transducer to change a direction of propagation of sound waves from one set for imaging by a remote operator.

In another alternative embodiment, the transducer array unit may be formed as a square or a rectangle and the linear transducer array in addition to rotation, twist or direction of sound wave transmission may move under remote motor control in a lengthwise direction from one end of a square or rectangular shaped housing to the other. In another embodiment as described above, the array may move in two perpendicular directions, for example, in an x or y axis direction on the body surface and not be permitted to rotate. Such a device may comprise a single transducer element or a linear array. On the other hand, a transducer array, for example, contained in a square or rectangular housing may also be rotatable to a predetermined angle of rotation by remote control at each incremental lengthwise or widthwise position and/or twisted. For example, such a transducer array unit may be used to monitor a fetus within a patient as it moves within the abdominal cavity. One unit may be fixed to a female patient's body and be manipulated alone or in conjunction with another or plural remotely manipulatable transducer units affixed to the female patient's body.

In an alternative embodiment and in conjunction with an imaging catheter as described in my co-pending U.S. patent application Ser. No. 11/782,991, filed Jul. 25, 2007, one or more remotely manipulatable transducer units may be used together with the imaging catheter to provide additional imaging of a minimally invasive heart operation or other procedure being performed on a patient in an operating arena. In deed visualization of any body part is possible including the heart, liver, kidney, brain, prostrate, any vascular structure, gland (such as the thyroid), extremity (knee replacement) or other body part to be monitored. For example, the remotely manipulatable wireless transducer unit may facilitate any intervention requiring ultrasound guidance including but not limited to entry into various body spaces such as pleural, peritoneal and pericardial space thus allowing therapy delivery, intervention, placement of devices such as pacemakers or medicine pumps and diagnostics. In addition to an imaging catheter, one or more remotely manipulatable wireless transducer array units may be used with another interventional, therapeutic or diagnostic system such as a biopsy forceps, a drainage catheter, a pressure monitoring system, a suture application system, a therapy delivery system or other interventional, therapeutic or diagnostic system known in the art.

In yet another embodiment, the remotely manipulatable transducer array unit may deliver ultrasound energy for therapeutic rather than imaging purposes, for example, to specific locations on or under the skin surface or within the body. During an interventional or a therapeutic procedure, the interventional procedure requiring intermittent ultrasound monitoring such as surgery or cardiac catheterization, the transducer can remain on the body during the entire procedure and the imaging or therapeutic treatment performed as and when needed by the remote operator. The remote operator may communicate with a surgeon or other operating room personnel by telecommunications to, for example, report that a medicine pump has been properly placed and is operating, for example, via a headset worn by the surgeon or other operating room personnel within an operating room.

The remotely manipulatable wireless transducer array unit communicates with a remote workstation that may include at least one display and a user interface screen for not only viewing an imaged area but, for example, a compartmentalized image area of a plurality of image displays of a region of interest and additionally present a user interface providing, for example, time of day, rotational degree and other control feedback in conjunction with usage of a control device such as a trackball or mouse. Other known controls such as on/off, depth, gain, focus and the like make be provided via conventional buttons, knobs or monitor screen controls. The work station may comprise one or a plurality of displays of the transmitted image of a region of interest including a three dimensional display or plural displays of multiple planes or a display showing manipulation of the ultrasound transducer element within the boundaries of a housing as placed on a patient and/or a display of operating parameters such as the coordinates of location of the transducer, its angle of rotation and its twist or angle of sound transmission. If plural transducer units are utilized, the single work station may provide additional displays for each remotely controlled and manipulatable transducer unit.

A first remote work station may communicate with a second remote work station by wired or wireless means and the second remote work station may serve as a back-up to the first remote work station in another embodiment. An operating room can only efficiently contain so many people assisting a surgeon and so much equipment. For example, the primary area of use of a wireless remote transducer unit may be within a fluoroscopy suite or an operating room such that one or more remotely manipulatable wireless remote transducer units communicates with a primary work station and/or a secondary remote work station outside the suite or room. In such a situation, it is convenient if each of the primary and secondary work stations are uniquely identified as are the wireless transducer units and only one work station is able to remotely control one wireless remote transducer unit at a time while the other may be afforded monitoring privileges. As suggested above, a control operator of a work station may communicate with the surgeon by means of a headset to answer questions a surgeon or other operating room personnel may have as a yes or no or advise of a successful procedure.

These and other embodiments and aspects will now be described with reference to the drawings and the detailed description to follow.

BRIEF DESCRIPTION OF THE DRAWINGS

FIG. 4a provides an exemplary signal content format for providing motor control of a remotely manipulatable transducer or transducer array of FIG. 1, 2 or 3 in a direction from a work station to a remote wired or wireless transducer including a unique transducer transceiver identifier if wireless or telecommunications transmission is utilized. The format also provides for known control such as on/off, focus, depth, mode and the like.

DETAILED DESCRIPTION OF THE EMBODIMENTS

Figure 1A:
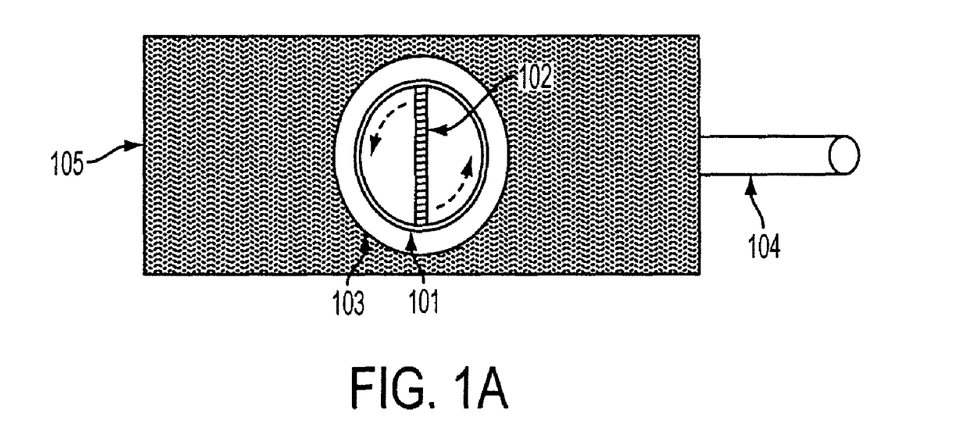
FIG. 1 comprises a top view and side view of a first plurality of embodiments and aspects of a multi-plane transducer unit comprising a rotatable linear array of transducer elements including a housing for mounting by securing material to a body of, for example, a patient or victim, which may be controllably rotated and otherwise controlled by wired or wireless signals remotely from the patient without an operator needing to be proximate to the body to manipulate or control the transducer elements or the housing.
Figure 1B:
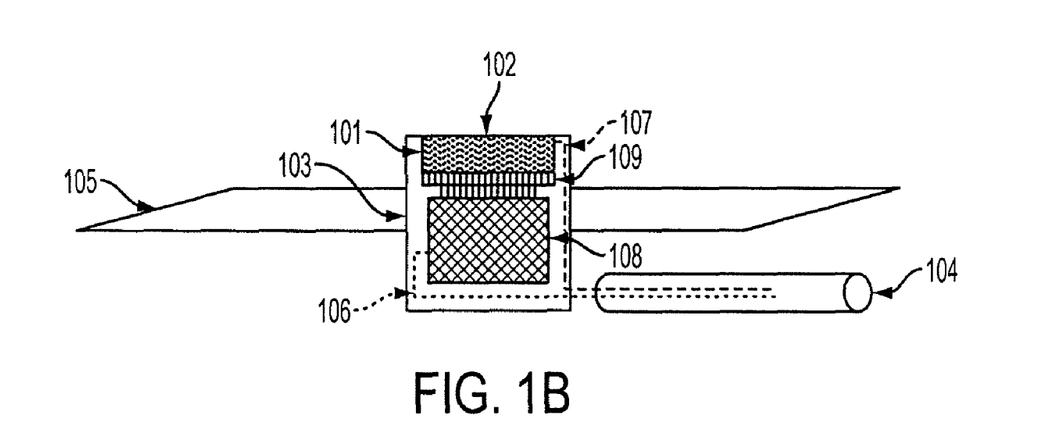

FIG. 1 comprises a top view and side view of a first plurality of embodiments and aspects of a multi-plane transducer unit comprising a rotatable linear array of transducer elements including a housing. The housing may be mounted by securing material to a body of, for example, a patient or victim. The transducer array or element may be remotely controllably rotated and otherwise remotely controlled by wired or wireless signals transmitted toward the array from a remote work station. An operator need not be proximate the patient's body to manipulate or control the transducer elements or housing. Similar reference numbers will be used throughout the detailed description to refer to similar elements wherein the first number of the reference number denotes the figure in which an element first appears. Transducer 101 may comprise a single transducer element for ultrasonic transmission and reception of reflected sound waves or a linear array 102 of transducer elements mounted, for example, in a circular manner from a top perspective as a diameter of the circle or at the center of the circle comprising housing 103. An arrow indicates an angle of rotation in a counter-clockwise direction of the transducer element or a linear array 102 within housing 103. Typically, an angle of rotation of 180 degrees when used with a linear array 102 will permit the collection of a plurality of image planes, for example, of the heart over which the array within housing 103 may be located and fixed to the body surface, in this case, a cylindrical housing as seen from top and side views forming a circular footprint on the body surface. The housing 103 is fixed to the surface of a human body, for example, in a position at the center of the chest to monitor the heart immediately below. The top surface of the side view shows transducer 101 which may rotate within the housing 103. The top surface of housing 103 intended to be fixed to a patient contains an impedance matching substance which may be complimentary to the application of a suitable impedance matching gel. Fastening or securing material 105 is shown in top and side views for fixing the housing to a human body skin surface with the transducer/impedance matching surface facing the human body surface. Within the housing 103 is also contained at least one motor, in the embodiment of FIG. 1, a motor 108 for rotating a transducer element or linear array 102. Also located within the housing 103, for example, in the vicinity of the motor may be a wireless transceiver and antenna (not shown; see, for example, FIG. 2) and other circuitry as necessary for receiving motor control signals and other known control signals such as on/off, mode, depth, focus and the like. Also, not shown is a battery or power system for powering the motors and circuits requiring power. Alternatively to a wireless device, housing 103 may have a control cable or wire 104 for transducer output, power, motor control and the like.

Cable 104 may lead to a work station console, preferably remote from a patient bedside and operate in a similar manner to known cables used with devices such as Toshiba PowerVision™ ultrasound machine, the difference being that the depicted cable further includes a rotation motor control lead or leads or a data line of such cable further incorporates motor control data in a serial data stream. Cable 104 may include motor wiring 106 to rotation motor 108 for control and power purposes. Cable 104 may further comprise transducer wiring 107 for power, control and image collection purposes.

As will be described herein, further motors 108 may be provided for twisting linear array 102 to permit a different direction of sound wave emission and/or reception, and for providing two directions, for example, lengthwise and widthwise (x and y) axis movement in the plane of the human body surface and according to how a rectangularly shaped housing 103 is placed on the body, i.e. an x and y axis are considered in relation to the housing. The housing 103 may be mounted at an angle (see, for example, manner of fixation 501 or 502 of FIG. 5 to the human body). Motor 108 may comprise an optional gear assembly 109 for more accurate, for example, incremental movement of array 102. Motor 108 is preferably a micro or miniature linear motor known in the art for turning a rotor and optional gear assembly for rotating the coupled transducer element or linear array 102 at incremental steps such as one degree steps from a vertical or horizontal orientation (vertical shown) through 180 degrees—clockwise or counterclockwise. In this manner, a linear array 102 may capture 180 different planes of view of, for example, a heart under observation, and a three dimensional view may be constructed using known software data analysis processes. Of course, the three dimensional analysis is improved and made stereoscopic if pairs (or more than two arrays) of devices at different observation locations according to FIG. 1 are used as will be described in conjunction with a discussion of FIG. 7. A transceiver (not shown) or a cable 104 may report the actual position of the linear array to a remote work station (not shown) as a value, for example, between 0 and 180 degrees.

Typical sizes for a cylindrical transducer housing 103 as shown in FIG. 1 may be from 1 cm in diameter to 3 cm in diameter. The height of the cylindrical housing may be similar or less than 1.5 cm.

Figure 3:
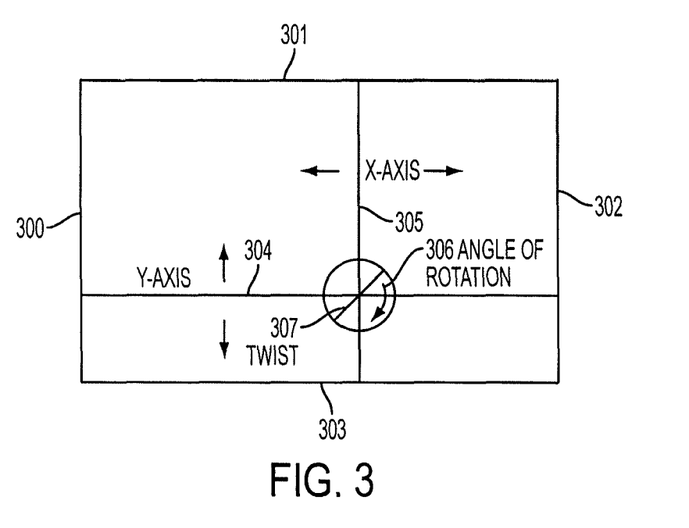
FIG. 3 provides an overview of a mechanical arrangement to be contained within a housing of embodiments of a transducer assembly unit for manipulating a transducer or linear transducer array in two perpendicular directions, for example, along an x axis and a y axis, to provide an angle of rotation to permit multiple image planes and a twist angle to redirect a sound wave emitted by a transducer or linear array of transducer elements whereby it is envisioned that a footprint on a patient body surface is rectangular or square and relates to the embodiments and circuits of FIGS. 1 and 2.

If a housing has a rectangular shape, for example, for observation of a fetus (see FIG. 6), its shape may be one the order of size of 10 cm by 12 cm, in which case, linear motors are provided for two directions, for example, x and y axis manipulation of the transducer array in addition to rotation. Referring briefly to FIG. 3, the surface proximate to the body of a housing 103 may comprise a rectangular shape and linear motors may move small rods carrying, for example, a transducer array to a particular x, y coordinate ranging from 0 to 10 cm in one direction to 0 to 12 cm in the other direction within its footprint on the body surface in incremental steps, for example of 5 mm. In a further embodiment as described above, a motor may be provided and mounted to twist a linear array as well as provide an incremental angle of rotation, again, within a range of 0 to 180 degrees with a default position at 90 degrees, or directly pointing sound waves into the human body.

Figure 2:
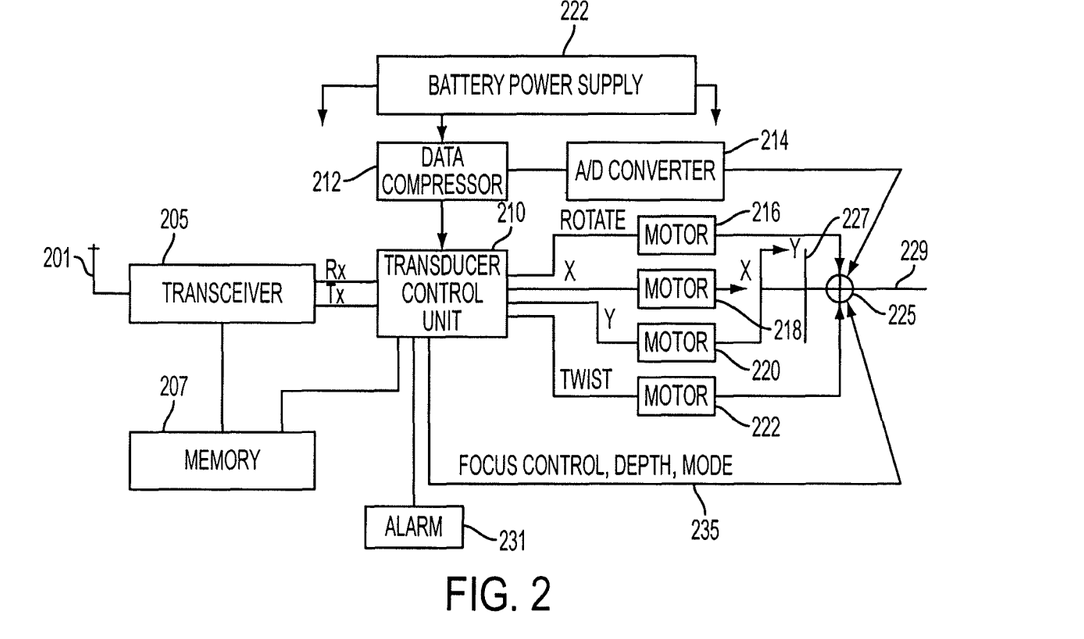
FIG. 2 provides a schematic block diagram for embodiments and aspects of a device as shown in FIG. 1 which may be wireless and further including a transceiver in addition to a transducer control unit. Also shown are a battery power supply, at least one motor for rotating a linear transducer element array, the linear transducer element array and analog to digital circuitry for converting collected image data to digital form for transmission via the transceiver.

FIG. 2 provides a schematic block diagram for embodiments and aspects of a wireless device as shown in FIG. 1 including a transceiver (which may be a wireless telecommunications transceiver), a transducer control unit, a battery, at least one motor for rotating a linear transducer element array, the linear transducer element array and analog to digital circuitry for converting collected image data to digital form for transmission via the transceiver. In FIG. 2, a wireless embodiment of a remotely manipulatable ultrasound transducer is assumed. Battery supply unit 222 is preferably a rechargeable lithium battery known in the art that powers all units requiring power within a housing 103.

Figure 4A:
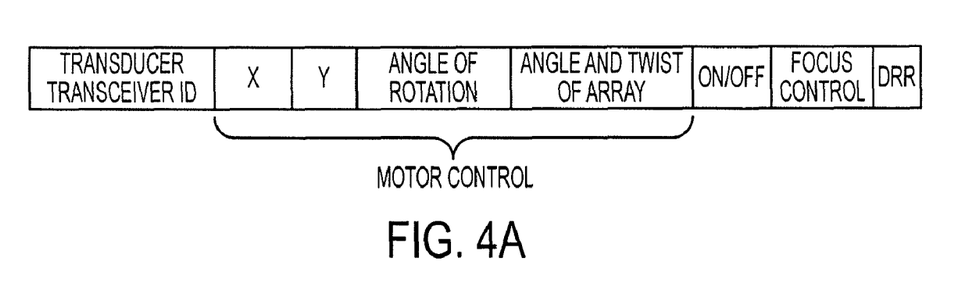
Figure 4B:
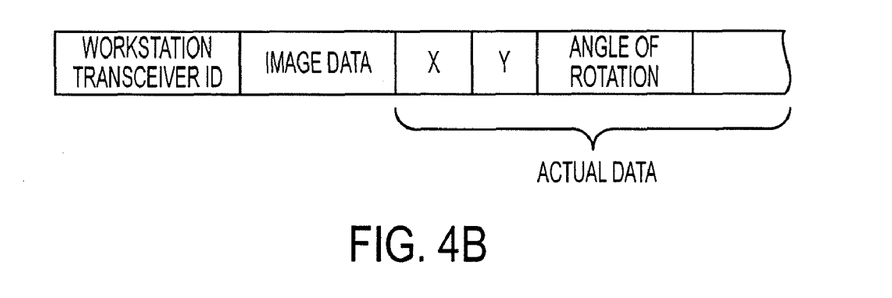
FIG. 4b provides an exemplary signal content format for providing a reply signal from a transducer or transducer array of FIG. 1, 2 or 3 in a direction from a remote wired or wireless transducer including a unique work station identifier if wireless or telecommunications transmission is utilized. The depicted format provides for feedback of actual location data of the position of the transducer or transducer array.

Transceiver 205 is an alternative to a control cable 104 for transmitting and receiving information and may receive and transmit a digital data signal generally in keeping with FIGS. 4a and 4b via antenna 201. While these figures depict what may be construed as a serial data stream, the depicted data may be sent in parallel or serial format and in any order including the order shown. Known telecommunications protocols may be utilized if the transceiver transmits and receives by radio frequency signal such as WiFi, blue tooth, Wimax and the like for a wireless local area network. As is known in the art, infrared and ultrasound may be used as well as other light frequencies than infrared. On the other hand, light waves are typically incapable of penetrating through walls and require a line of site transmission path. Yet, by way of example, light wave transmission is feasible; for example, a light wave transceiver connected to a work station may be mounted, for example, in the ceiling of an operating arena and a unit mounted to a patient facing upward may communicate with the ceiling mounted unit in a line of site. As described above, since a cable 104 provides a direct link to a remote work station, cable 104 need not necessarily transmit data uniquely indicative of a given transmitter, transducer or work station because the cable 104 may comprise a direct link between known devices. If any other device is connected to cable 104, then addressing using a unique address (or telephone number) or other identifier should be used for a connected device. Transceiver 205 may receive a data signal from a work station, demodulate the signal and output a demodulated baseband data signal including data per FIG. 4a to controller 210 which may be a microprocessor, application specific integrated circuit or other control circuit which may be designed and fabricated in a manner well known in the art. In the other direction of transmission, the transceiver 205 may receive image data for one or more planes or sequential images and other signal including actual position data per FIG. 4b from controller 210 for transmission to a uniquely identified remote work station.

Following the path of a received signal at antenna 205, the received signal may be received at radio frequency at transceiver 205, demodulated and a Rx data output signal passed to controller 210 for processing. Controller 210 authenticates the signal as directed to it by means of the transmitted unique transducer identification code of FIG. 4a. In addition, the signal may require processing in accordance with well known protocols for decompression, decryption, parity and other data error detection and correction algorithms and the like (not shown). In one embodiment, for example, for multi-planar imaging purposes, the transducer array 225 is linear and may be rotated. A rotate signal which may indicate an angle between 0 and 180 degrees in incremental steps of, for example, one to five degrees can indicate rotation in a clockwise or counterclockwise direction or indicate an angle to which the transducer array or element is to be rotated (for example, from 90 degrees, actual present position, to 120 degrees, desired position) is received and passed to linear motor 216 having a rotor for rotation using, possibly, an optional gear assembly 109 for turning the linear array 102 to a desired angle of rotation.

In an alternative embodiment, for example, for therapeutic purposes, a direction of sound wave propagation, depth and the like signal are received and reported to actuate twist motor 222 to a desired angle of twist in addition to a desired angle of rotation via motor 216 to, for example, deliver a therapeutic sound wave to a given body organ or sub-tissue layer at a given transmitted depth, for example, represented by a sound wave power level, within the patient's body from the transducer 102, 225. In an embodiment paired with another unit, the angle of twist and rotation may be synchronized so that one transducer array 102 may cooperate with another transducer array as sound wave transmitter and sound wave receiver for together providing image data either individually or together.

In a further alternative embodiment, the transducer array 102 or transducer element may be manipulated in two directions, perpendicular to one another, along the patient's body surface, denoted an x direction and a perpendicular y direction or axis as shown in FIG. 3. The transceiver 205 outputs such control data to controller 210 which then actuates motors 218 for x axis movement and 220 for y axis movement of transducer element or transducer array 102, 225 as shown in FIG. 3. Also shown in FIG. 2 are x, y axis 227, 229 which are controlled by motors 218, 220. When arriving at the x,y position of interest, the transducer 102, 225 may be rotated or twisted or rotation and/or twisting/rotation may occur en route to the x,y position of interest. Feedback to the remote work station may be provided via actual data indicating all parameter values of interest, on/off, focus level, depth, x axis, y axis, angle of rotation and angle of twist (most of which are shown in FIG. 4b).

Also, controller 210 may be in receipt of off/on, focus control, mode, depth and other control data which is passed to transducer 102, 225 for proper operation, for example, to regulate the amount of power delivered to transducers for sound wave emission or for focusing the array. This control lead or collection of leads is shown as data line 235.

The output of transducer array 102, 225 may be raw image (reflected sound wave) data similar to that obtained by a hand-held transducer array known in the art. It may be in analog form and provided to an A/D converter 214 for sampling at an appropriate sampling level. The data signal output of A/D converter 214 may be further compressed at data compressor 212 prior to formatting at controller 210 for transmission at transceiver 205 and/or storage at memory 207. These circuits 214 and 212 are shown as separate circuits but may, together with controller 210 be in the form of a single application specific integrated circuit (ASIC) or provided as separate circuits. Memory 207 may be on board a microprocessor chip or provided separately. In one embodiment, memory 207 may comprise a removable memory for uploading data to a device for telecommunications transmission. The image and other data prior to transmission or for long term storage may be temporarily or more permanently stored in memory 207. Similarly, memory 207 may be utilized for temporarily storing control data as received from transceiver 205 and prior to being operated on by controller 210. In one embodiment as will be described herein, there is no data transmission via cable or wireless means.

Image and associated position data and the like for a given image along with time of day and date may be stored in a fanny pack or personal remote control device worn or otherwise carried by the patient. This assumes a time of day and date clock associated with controller 210 or the time and day may be periodically updated via a transmission to the unit of FIG. 2. In, for example, a therapeutic embodiment of a remotely manipulatable transducer array, the patient wearing or carrying the device may control delivery of therapeutic sound waves via a transducer array 102 and control the direction and depth of transmission. For example, ultrasound has been found to assist in relieving arthritis and other pain, for example, in a hip, shoulder, knee or other joint.

In one embodiment where the circuitry and motors are contained in a housing and in accordance with FIGS. 1, 2, 3 and 4, the housing is worn by a person, the person may be remotely observed as they go about their daily routine. For example, a remotely manipulatable ultrasound transducer array located so as to monitor a major organ may detect a change that requires medical attention. In such an instance, alarm 231 may comprise a vibrator or display or other alarm device to signal the wearer to report to a facility. The alarm may also indicate a point in time when a memory 207 is full of un-transmitted images, and the wearer must change their memory card of memory 207 or report to a work station or other telecommunications facility for image data upload.

FIG. 3 provides an overview of a mechanical arrangement to be contained within a housing 103 of rectangular or square embodiments of a transducer unit for manipulating a transducer or linear transducer array in two directions, for example, along an x axis and a y axis and to provide an angle of rotation and a twist angle at a desired x, y coordinate pair to redirect a sound wave emitted by a transducer or linear array of transducer elements whereby it is envisioned that a footprint on a patient body surface is rectangular or square and relates to the embodiments and circuits of FIGS. 1 and 2. Assume the rectangle housing comprises guide wires or rods 300, 301, 302 and 303 on which are provided y-axis rod 304 which may be moved in an up and down direction shown via a corresponding motor 220 and gear assembly not shown to incremental steps along the y axis. Similarly, there is provided x-axis rod 305 which may be moved to the left or the right direction shown via corresponding motor 218 and a gear assembly not shown. X-axis rod 305 and Y-axis rod intersect at a desired point where an array or element may be affixed via further motors 216, 222. For example, rotor 306 of motor 216 (in combination with an optional gear assembly 109) provides rotation of a mounted transducer array 102, 225 or transducer element to a predetermined or desired angle of rotation. Motor 222 provides twist 307 to linear array or element 102 to change direction of sound wave transmission or reception with 90 degrees—straight down—being a default position for twist.

FIG. 4a provides an exemplary signal content format for providing motor control of a transducer or transducer array of FIG. 1, 2 or 3 in a direction from a work station to a remote wired or wireless transducer including a unique transducer transceiver identifier if wireless transmission is utilized. The format also provides for known control such as on/off, focus, depth, mode and the like. Other control data may come to mind of one of ordinary skill in the art of ultrasound apparatus. Motor control data may be transmitted, for example, in the form of ultimate desired position or as an incremental step from an actual position or other way that may come to mind of one of skill in the art.

FIG. 4b provides an exemplary signal content format for providing a reply signal from a transducer or transducer array of FIG. 1, 2 or 3 in a direction from a remote wired or wireless transducer including a unique work station identifier if wireless transmission is utilized. The format provides for feedback of actual location data of the position of the transducer or transducer array. The actual location data may be compared to a desired location to determine if the remotely manipulatable transducer or transducer array has reached a desired position so that imaging may begin.

Figure 5:
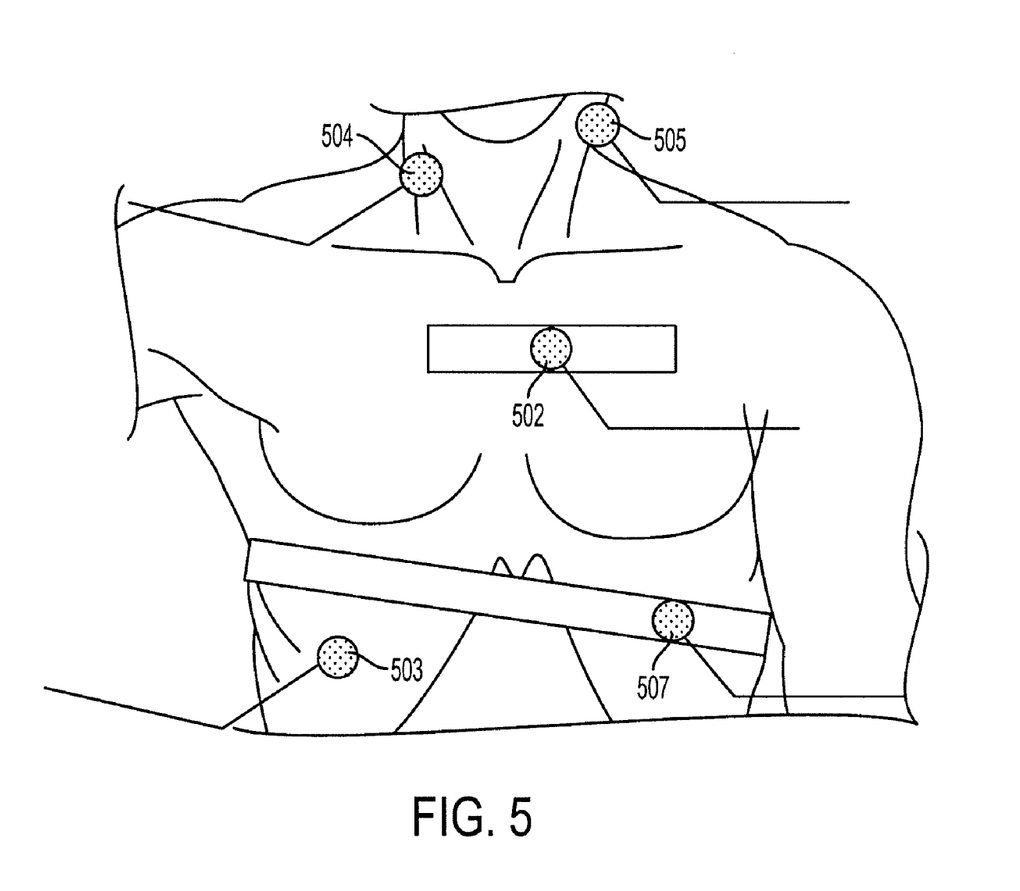
FIG. 5 provides a plurality of suggested locations on a human body for locating a remotely manipulatable transducer or transducer array whereby the units may comprise devices and adhesive material similar to electrodes used in electrocardiography, banded adhesive attachment or bandage or banding of the manipulatable transducer or transducer array housing to a human patient's body.

FIG. 5 provides a plurality of suggested locations on a human body for locating a remotely manipulatable ultrasound transducer or transducer array whereby the units may comprise housings and utilize adhesive material similar to materials used for applying electrodes to a human body as used in electrocardiography. Also, banded adhesive attachments to housings or bandage or banding of the manipulatable transducer or transducer array housing to the human body may be provided. No position on the human body should be considered to be excluded from reach by a remotely manipulatable transducer or transducer array. Fixing material for a given position on the patient's body is well known in the field of bandaging from first responder training in medical emergencies and the like.

Image locations 507 and 502 may be used in combination to provide image locations for the heart and develop three dimensional images thereof in multiple planes. Location 503 may be used to image the liver. Image location 504 may be used to image the carotid artery or neck structure or any gland within the neck. Image location 505 may be used to image trans-cranial structures including blood vessels. The fixing material may be a band as in 507 or adhesive tape material as in 502 or affixed via an adhesive as in 503, 504 or 505.

Figure 6:
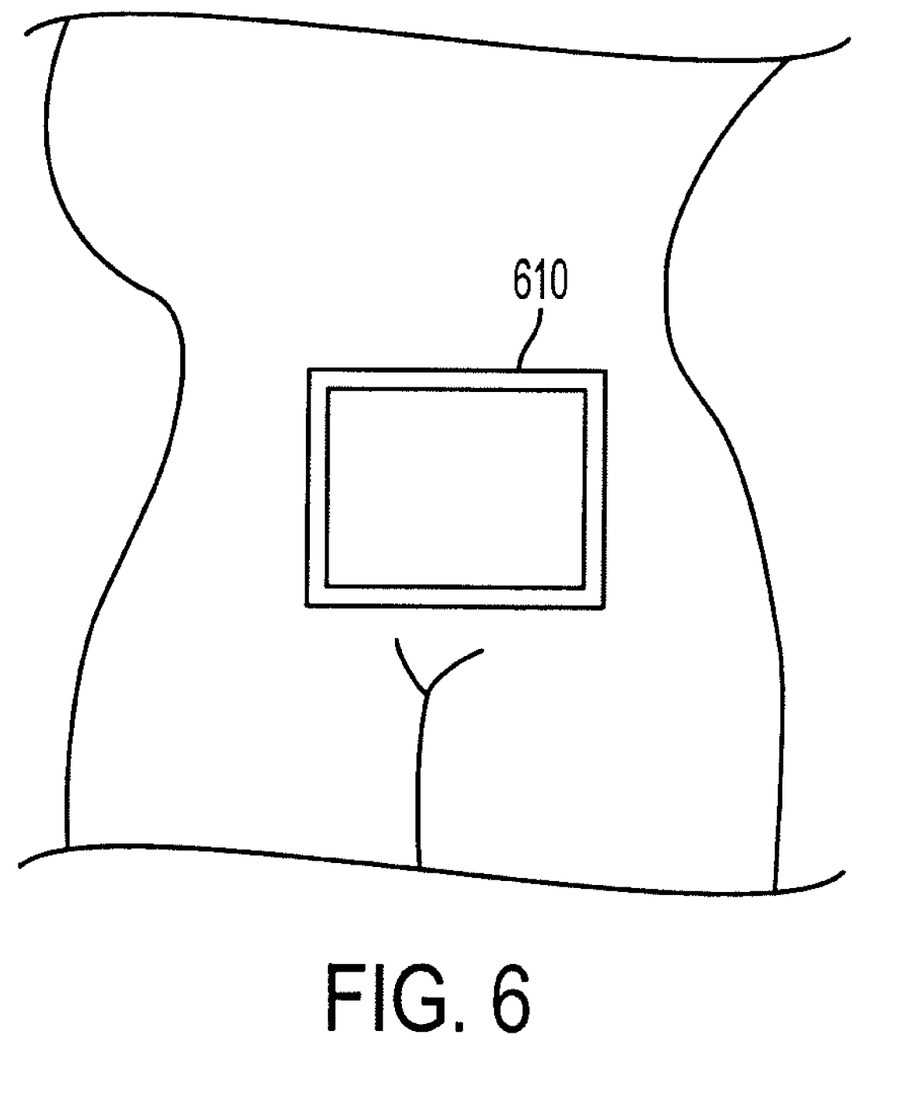
FIG. 6 provides an exemplary application of a manipulatable transducer array that may be worn by a pregnant female in the abdominal area for remotely monitoring a fetus for, for example, extraordinary conditions.

Now some specific applications of the remotely manipulatable ultrasonic transducer apparatus of FIGS. 1-5 will now be discussed with reference to FIGS. 6 and 7. FIG. 6 represents a fetus imaging and FIG. 7 an imaging during a heart operation.

Fetus Monitor

FIG. 6 provides an exemplary application of a manipulatable transducer array that may be worn by a pregnant female in the abdominal area for remotely monitoring a fetus for, for example, extraordinary conditions. Let us assume that a female patient has been checked into a maternity ward of a hospital. A rectangular, remotely manipulatable transducer array may be affixed as shown in FIG. 6 by adhesive to the abdominal cavity and appropriately be provided with a surface that is sufficiently curved as to maintain contact with a, for example, 10 cm by 12 centimeter rectangular region of interest. For example, such surface of the housing 103 may be made of a giving material such as rubber and the transducer assembly contained within the housing at sufficient depth to permit the curved skin surface to be absorbed within a curved surface and maintain constant skin contact. The patient typically is prone to considerable movement during pre-birth and requires considerable attention. The housing must be firmly secured by adhesive material. Fetus monitoring equipment may be used in concert with the transducer array and the fetus remotely monitored for activity such as turning or stage of birth canal entry and passage via the remotely manipulatable transducer or transducer array shown. Typically, bed-side space is at a premium as the father or other coach and nurses are present at bedside. Also, periodically, a physician or surgeon will want to check the degree of opening of the birth canal for delivery. A rectangular housing 610 affixed as shown in FIG. 6 permits remote monitoring of a fetus during pre-birth and birth from a remote work station, saving valuable bed-side space and providing an invaluable supplement to normal fetus monitoring devices, for example, for monitoring fetus heart rate and pressure.

Minimally-Invasive Pericardial Surgery

Figure 7:
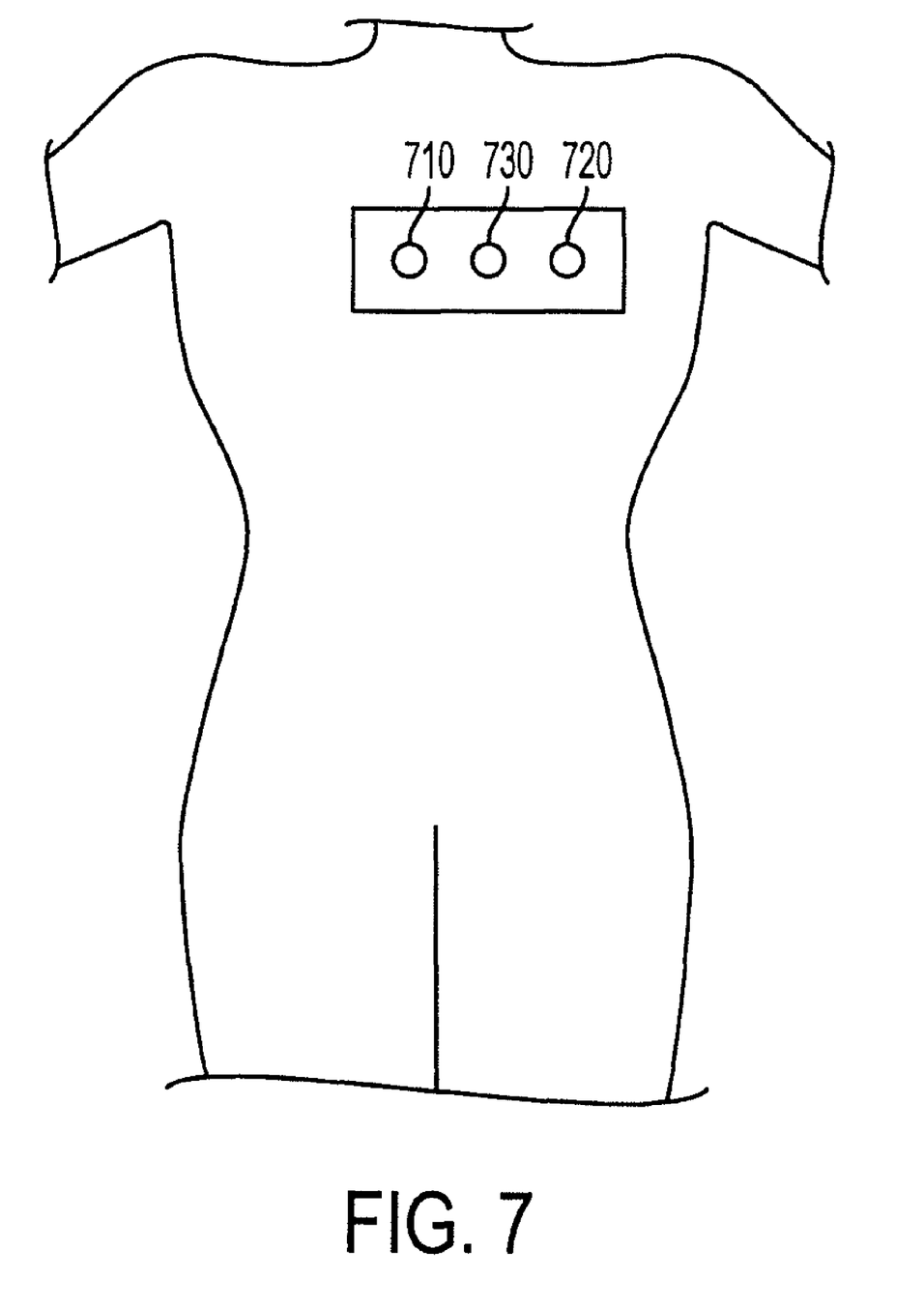
FIG. 7 shows an arrangement for pericardial activity and possibly surgery including first and second manipulatable transducer units mounted to either side of, for example, an image guided catheter surgical location as one example of an application for minimally invasive heart surgery.

FIG. 7 shows an arrangement for pericardial activity and possibly surgery including first and second remotely manipulatable transducer units, 710, 730 mounted to either side of, for example, an image guided catheter 720 surgical location as one example of an application for minimally invasive heart surgery. The image guided catheter may be one as shown and described in my co-pending U.S. patent application Ser. No. 11/782,991, filed Jul. 25, 2007, entitled "Image Guided Catheters and Methods of Use," of the same inventor, for example, per FIG. 1 of that application, incorporated herein by reference as to its entire contents. Methods of use include, for example, double balloon heart wall processes, cavity drainage and the like wherein the wireless arrays 710, 730 may image successful deployment of the image guided catheter and intervention, therapeutic or diagnostic apparatus in the region of interest of the heart. Elements or transducer arrays 710, 730 may cooperate to provide stereoscopic as well as multi-planar imaging while the image-guided catheter contains its own ultrasonic array for imaging a point of intervention, therapeutic or diagnostic care.

A work station for use with such an arrangement shown in FIG. 7 may comprise a plurality of screens to show all images obtained from each of ultrasound transducer elements or arrays 710, 720 and 730. An operator remote from the operating suite may remotely manipulate and control arrays 710, 730 and obtain imaging therefrom. The work station operator may communicate with a surgeon by a wireless telecommunications device worn, for example, as a headset by each of the surgeon (or other operating room personnel) and the work station operator. The transducers may be manipulated remotely within a region of interest remotely from the work station and remain on the patient during the entire operation. The imaging can occur when and as requested by the surgeon of the work station operator. Uses may comprise, for example, but not be limited to pericardiocentesis, vascular surgery, coronary angioplasty, valvuloplasty, alcohol septal ablation, delivery of drugs, stem cells or laser therapy, valve repair or replacement, cardiac shape modifying devices such as ACORN-like or MYOSPLINT™, myocardial scar reconstruction, ventricular reconstruction and ventricular assist device placement. One may monitor the blood flow of any vessel to and from the heart or carotid blood flow during cranial or other surgery. Besides the image guided catheter, other devices usable with a remotely manipulatable transducer or transducer array include a biopsy forceps, a drainage catheter, a pressure monitoring system, a suture application system, a therapy delivery catheter or system or other intervention system.

Figure 8:
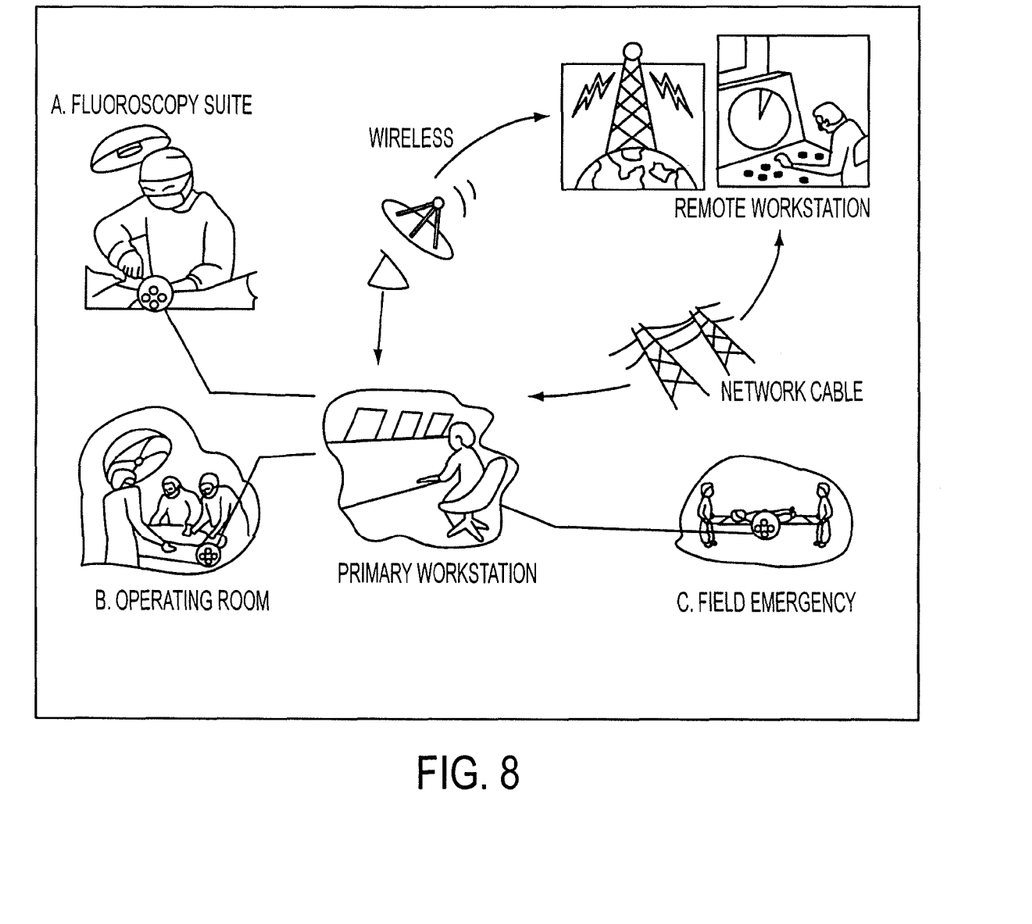
FIG. 8 shows a workflow scenario whereby the primary workstation is remote from a fluoroscopy suite, operating room and the like and, if necessary, shielded from adverse impacts of radiation such as magnetic resonance.

FIG. 8 shows a workflow scenario whereby the primary workstation is remote from a fluoroscopy, operating room and the like and, if necessary, shielded from adverse impacts of radiation such as magnetic resonance. One further limitation of using ultrasound in an operating suite is electrocautery procedures which may degrade collected image signal quality when the electrocautery apparatus is in use. Referring to FIG. 8, there may be situations where the ultrasound operator be optimally protected, for example, in a fluoroscopy suite where the operator is exposed to radiation and would otherwise need a heavy lead suit. Even with the lead suit, the operator would typically have to move a 400 or 500 pound ultrasound machine back and forth from along side the operating table to away from the table when a C arm is being used. Now, the ultrasound operator may sit at a remote work station after placing the remotely manipulatable transducer or transducer array on the surgical patient and then sit behind a lead shield to manipulate and operate the transducer or linear transducer array remotely at their primary work station. Also, there is typically inadequate space in an operating room for an ultrasound operator, for example, next to a surgical operating table. The operator may place the transducer and then remotely manipulate and control and view images from the remotely manipulatable transducer. Their work station can be located in a corner of the operating room or outside the operating room and the operator communicate by telecommunications means with the surgeon (or other operating room personnel).

Figure 9:
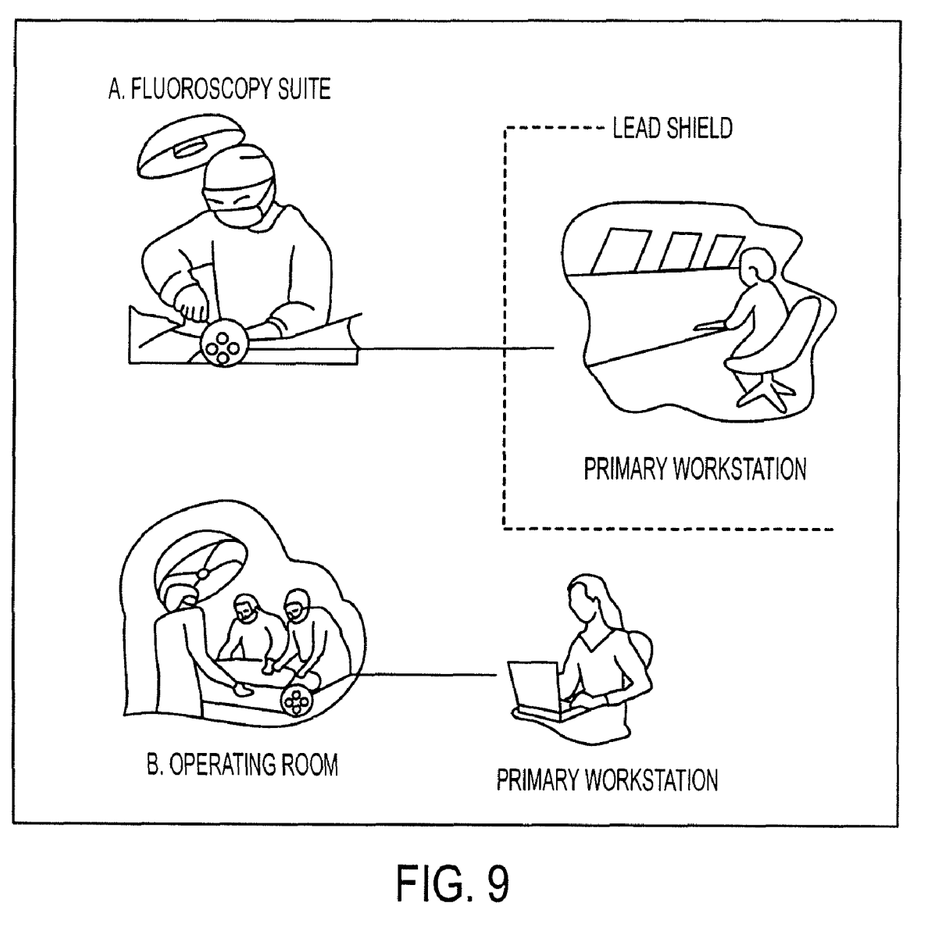
FIG. 9 shows another workflow scenario for describing, for example, remote field emergency use, operating room, fluoroscopy suite use and primary and alternative work stations connected by a wireless or wired telecommunications network.

FIG. 9 shows another workflow scenario for describing, for example, remote field emergency use, operating room, fluoroscopy suite use and primary and alternative work stations connected by a wireless or wired network such as a telecommunications network. Regardless of the patient location, even if the patient is considered a field emergency, the remotely manipulatable transducer may be placed by an emergency first responder, remotely manipulated to a desired location on the patient body surface and image data remotely transmitted to a remote work station. The emergency first responder can respond to simple commands to appropriately place one or more transducers on the victim, for example, via a telecommunications channel. For example, first responder personnel at a remote location in Alaska where there is a medical emergency can be remotely guided by a hospital in Juneau to properly place a remotely manipulatable transducer or transducer array at a location on the body surface, and the image data may be conveyed by satellite telecommunications to Juneau as control data is transmitted on the reverse path from a remote operator/manipulator. A second communications channel may used by the operator to guide the first responder as to the proper placement of the remotely manipulatable transducer or transducer array. Thereafter, the remote operator in Juneau may move the array remotely and control the diagnostic, therapeutic or interventional imaging.

These and other features of embodiments and aspects of a remotely manipulatable ultrasound transducer or transducer array may come to mind from reading the above detailed description and any claimed invention should be only deemed limited by the scope of the claims to follow.

What I claim is:

1. A remotely manipulatable ultrasound transducer assembly for wirelessly communicating with a remote work station including a display, the transducer assembly comprising
    a transducer array for collecting multi-planar ultrasound images,
    a first motor for rotating the transducer array in a plane parallel to the human body about a point, the remotely manipulatable transducer array configured to be fixed to a human body surface,
    a second motor for twisting the transducer array about a line of the transducer array from a default position and the transducer array, responsive to the second motor, configured to direct ultrasound waves directly into the human body to which the transducer array is fixed to other planes below skin surface from the line of the transducer array;
    a third x axis motor and a fourth y axis motor configured to move the transducer array in two directions within a two-dimensional footprint on the human body surface;
    a transceiver for communicating wirelessly with the remote work station;
    a controller for receiving motor control data from said transceiver and controlling said first, second, third and fourth motors responsive to receipt of motor control data to relocate said transceiver array; and
    a housing for the transducer array and the first, second, third and fourth motors, the housing having a relatively flat surface configured for fixation to a two-dimensional footprint of the human body surface.

2. The remotely manipulatable transducer assembly as recited in claim 1 further comprising
    a second motor for twisting the transducer array from a default position directing sound waves directly into the human body to which it is fixed to other positions for directing sound waves below skin surface.

3. The remotely manipulatable transducer assembly as recited in claim 2 further comprising
    an x axis motor and a y axis motor for moving said transducer array in two directions within a two-dimensional footprint of the housing on the human body surface.

4. The remotely manipulatable transducer assembly as recited in claim 1 further comprising
    an x axis motor and a y axis motor for moving said transducer array in two directions within a two-dimensional footprint of the housing on the human body surface.

5. The remotely manipulatable transducer assembly as recited in claim 1 for cooperating with a second such assembly configured to be fixed to the same human body to provide three dimensional, stereoscopic imaging of a region of interest.

6. The remotely manipulatable transducer assembly as recited in claim 1 for cooperating with an image guided catheter, the image guided catheter for use in minimally invasive surgical procedures for therapeutic, diagnostic or interventional purposes.

7. The remotely manipulatable transducer assembly as recited in claim 1 further comprising a battery power supply for powering elements of the transducer assembly requiring power.

8. The remotely manipulatable transducer assembly as recited in claim 1 further comprising
a battery power supply for powering elements of the transducer assembly requiring power and
a memory for temporary storage of image data from said transducer array.

9. The remotely manipulatable transducer assembly as recited in claim 8 further comprising
a triggerable alarm for signaling a user of a predetermined condition.

10. The remotely manipulatable transducer assembly as recited in claim 1 having dimensions appropriate for imaging a human fetus during birth,
the transducer assembly being remotely manipulatable and configured to image a birth canal,
the transducer assembly having a housing transducer surface configured to conform to a curved surface of a pregnant woman and adapted to be worn by the woman during pre-birth.

11. The remotely manipulatable transducer assembly as recited in claim 1
the housing containing a rod assembly in the form of a rectangle of two parallel pairs of rods,
each parallel pair of rods for conducting a perpendicular rod member in one of two directions,
the transducer assembly for connection to the juncture of two perpendicular rod members,
the two perpendicular rod members for movement as determined by the third x axis and fourth y axis motors.

12. The remotely manipulatable transducer assembly as recited in claim 1 further comprising
a wired remote control for use by a wearer of the assembly, the transceiver for receiving control signals and the transducer array configured for directing sound waves in a therapeutic manner to a region of interest, the control signals including a direction of sound wave transmission, an angle of rotation and a depth of transmission via said remote control.

13. The remotely manipulatable transducer assembly as recited in claim 1
said transceiver for wirelessly reporting actual position data of said transducer array to a remote work station.

14. A remotely manipulatable ultrasound transducer assembly for wirelessly communicating with a remote work station including a display, the transducer assembly comprising
at least one transducer element for collecting ultrasound images,
a first motor configured for mounting to a chest of a human body and for rotating the at least one transducer element about a point in a plane parallel to the human body when the remotely manipulatable transducer is fixed to a human body chest via a housing,
a second motor for twisting the at least one transducer element from a default position and configured for directing sound waves directly into the chest of the human body to which it is fixed to other positions below skin surface including one of the heart and one or the other of the lungs of the human body;
a third x axis motor and a fourth y axis motor configured for moving said at least one transducer element in two directions within a two-dimensional footprint of the housing on the chest of the human body;
a transceiver for wirelessly communicating with the remote work station,
a controller for receiving motor control data from said transceiver and controlling said first, second, third and fourth motors responsive to receipt of the motor control data to relocate said at least one transducer element; and
the housing for the at least one transducer element and the first, second, third and fourth motors, the housing having a relatively flat surface configured for fixation to the chest of the human body.

15. The remotely manipulatable transducer assembly as recited in claim 14 further comprising
a second motor for twisting at least one transducer element from a default position directing sound waves directly into the human body to which it is fixed to other positions for directing sound waves below skin surface.

16. The remotely manipulatable transducer assembly as recited in claim 15 further comprising
an x axis motor and a y axis motor for moving said at least one transducer element in two directions within a two-dimensional footprint of the housing on the human body surface.

17. The remotely manipulatable transducer assembly as recited in claim 14 further comprising
an x axis motor and a y axis motor for moving said at least one transducer element in two directions within a two-dimensional footprint of the housing on the human body surface.

18. The remotely manipulatable transducer assembly as recited in claim 14 for cooperating with a second such assembly when fixed to the same human body to provide three dimensional imaging of a region of interest.

19. The remotely manipulatable transducer assembly as recited in claim 14 for cooperating with an image guided catheter, the image guided catheter for use in minimally invasive surgical procedures.

20. The remotely manipulatable transducer assembly as recited in claim 14 further comprising
a battery power supply for powering elements of the transducer assembly requiring power.

21. The remotely manipulatable transducer assembly as recited in claim 14 further comprising
a battery power supply for powering elements of the transducer assembly requiring power and
a memory for temporary storage of image data from said at least one transducer element.

22. The remotely manipulatable transducer assembly as recited in claim 21 further comprising
a triggerable alarm configured for signaling a user of a predetermined condition.

23. The remotely manipulatable transducer assembly as recited in claim 14 wherein said at least one transducer element comprises an array of transducer elements, said array of transducer elements being one of a linear array, a conical array and a phased array.

24. The remotely manipulatable transducer assembly as recited in claim 14, the housing containing a rod assembly in the form of a rectangle,
each of a first and a second parallel pair of rods for conducting a perpendicular rod member in one of two directions,
the transducer assembly for connection to the juncture of two perpendicular rod members, and
the two perpendicular rod members for movement as determined by the third x axis and fourth y axis motors.

25. The remotely manipulatable transducer assembly as recited in claim 14, further comprising a wired remote control for use by a wearer of the assembly, the transceiver for receiving control signals and the at least one transducer element configured for directing sound waves in a therapeutic manner to a region of interest within a chest cavity of the human body, the control signals including a direction of sound wave transmission, an angle of rotation and a depth of transmission via said remote control.

26. The remotely manipulatable transducer assembly as recited in claim 14,
said transceiver for wirelessly reporting actual position data of said transducer array to a remote work station.

* * * * *